United States Patent

Re. 28,399

Reissued Apr. 29, 1975

28,399

INTRAUTERINE CONTRACEPTIVE METHOD

Jaime A. Zipper, Santiago, Chile, assignor to G. D. Searle & Co., Chicago, Ill.

No Drawing. Original No. 3,563,235, dated Feb. 16, 1971, Ser. No. 760,688, Sept. 18, 1968. Appplication for reissue Aug. 7, 1972, Ser. No. 278,434

Int. Cl. A61f *5/46*

U.S. Cl. 128—130 4 Claims

Matter enclosed in heavy brackets [ ] appears in the original patent but forms no part of this reissue specification; matter printed in italics indicates the additions made by reissue.

ABSTRACT OF THE DISCLOSURE

A method of contraception is disclosed characterized by providing for the presence of elemental copper or zinc in the uterine cavity. This invention is preferably practiced by wrapping a small amount of wire or foil or by placing a sleeve around a conventional intrauterine device prior to implantation. In a modification of this method, two different metals are employed to provide improved effectiveness.

This invention relates to an improved contraceptive method.

During recent past years, due to world population pressures, a vast amount of research has been undertaken directed to developing improved contraceptive methods. One such method which has gained wide favor because of its high effectiveness is to employ certain hormones known to modify the body endocrinology and suppress ovulation. These hormones, popularly administered as birth control pills, if used regularly, prove to be highly effective and reliable for controlling conception. Nevertheless, they are not without difficulties when used in large scale birth control programs in developed and in developing countries, not only because they are relatively expensive, but also because considerable reliance has to be placed upon the patient to take the pills in accordance with the prescribed regimen.

In view of these disadvantages of conventional birth control pills, the use of intrauterine contraceptive devices has achieved considerable popularity. Such devices may be inserted inexpensively in patients in large scale programs, and, moreover, do not require reliance upon a patient's willingness or ability to follow a particular regimen of treatment. Despite these advantages of the intrauterine contraceptive devices which are already available and being manufactured commercially, it has been found that they are not as effective as the so-called conventional birth control pills, provided the latter are used within the prescribed regimen. Accordingly, considerable effort has been directed toward improving the efficacy of intrauterine contraceptive devices.

In accordance with the present invention, it has been found that the presence of elemental copper or zinc in the uterine cavity is highly effective to prevent conception.

The elemental metal may be inerted or implanted in the uterine cavity by any convenient method. Normally, only a relatively small amount is required, for example, a small piece of copper or zinc wire in the order of one to two centimeters in length and a fracture of a millimeter in diameter is effective. The effectiveness of a given quantity of metal appears to be related to the exposed surface area. In general it is believed that an exposed metallic surface of at least about 20 square millimeters is sufficient. Larger amounts may be used so long as the size of the insert is not unacceptable.

Small quantities of foreign material in the uterine cavity, however, would not ordinarily have the desired longevity of action because they would be quickly expelled or sloughed off either through muscular uterine contractions or during the period of regular menstrual flow. Preferably, therefore, the elemental metal is implanted within the uterine cavity by means of a carrier, for which purpose any of the conventional intrauterine contraceptive devices are eminently suitable. A wide variety of such devices are known, i.e., single or multiple loops, spirals, crosses, and various sinuous shapes. The metal may be deposited onto the carrier in the following manners: (a) it could be in the form of wire which would be wound around a portion of the carrier; (b) the metal could be in the form of foil and could be wrapped around the carrier; (c) the metal could be in the form of tubing and could be slipped onto a portion of the carrier as a sleeve and swaged in place by pressure; (d) the metal could be applied to the carrier by means of a plating process; (e) metal filings, powder, etc. may be intimately blended with the resinous material from which the intrauterine device is made.

The elemental copper of zinc in the present invention may be used in the pure state, or it may be used in the form of a pharmaceutically acceptable alloy. Representative alloys which may be used include, but are not limited to, 98% copper, 2% nickel; 94% copper, 6% nickel; 88% copper, 12% nickel; 78% copper, 22% nickel; 55% copper, 45% nickel; bronzes and brasses containing from 5 to 35% zinc and from 95 to 65% copper, copper-silver alloys containing up to 90% silver; and copper-tin containing alloys such as certain admiralty metals and bronzes (which may also contain other alloying elements such as zinc, phosphorus, aluminum, manganese, etc.).

A modification of the present invention which has been found to improve effectiveness of the copper or zinc is to provide for the presence of a second dissimilar metal. The second metallic element appears to have a synergistic effect on the copper or zinc since bimetalic couples are even more effective as contraceptives. Any combination of a variety of pharmaceutically acceptable metals or alloys thereof may be used; for example, silver, stainless steel, gold, platinum, tin, brass, bronze, and the like. It will be obvious, moreover, that the combination of copper and zinc themselves can be used as a two-metal system for improving the efficiacy of the present invention.

The present invention may be further understood by reference to the following examples:

EXAMPLE 1

Comparative tests were performed on a group of patients to ascertain the relative effectiveness under clinical conditions of the presence of a small amount of copper in the form of wire carried on an intrauterine device. A "T" shaped plastic intrauterine device was placed in 250 members of the group as a control. In the control group no exogenous copper, zinc or other free elemental metal was present on the intrauterine device. In the balance of the group the same intrauterine device was used modified by winding a piece of copper wire, 3 centimeters in length and ¾ millimeters in diameter, around the stem of the "T." The occurrence of pregnancies was observed in these two groups as follows:

RESULTS OF IMPLANTATION OF INTRAUTERINE DEVICES PER 500 USERS

| Period of use and device | Pregnancies per 100 users | Expulsions | | Removals | |
|---|---|---|---|---|---|
| | | First | Later | Medical | Personal |
| Plastic "T", 9 months | 15.4 | 8.0 | 0.6 | 0.8 | 3.1 |
| Plastic "T" with copper wrapping, 9 months | 2.8 | 3.4 | 0.6 | 3.2 | 4.3 |
| Plastic "T", 6 months | 6.3 | 0.5 | 0.7 | 0.0 | 2.0 |
| Plastic "T" with copper wrapping, 6 months | 0.0 | 0.8 | 0.4 | 4.0 | 3.0 |

EXAMPLE 2

The contraceptive properties of metallic copper were determined in experimental animals in the following manner:

Adult virginal rabbits were used. In each instance, the left uterine horn served as the control and the right uterine horn served as the site of the intrauterine device.

Under general anesthesia an abdominal incision was made and a 1.5 cm. length of wire consisting of 4 strands of wire each of which was 0.15 mm. in diameter was inserted in the lower portion of the cavity of the right uterine horn close to the cervical os. The wire was fastened in place by a silk suture through the myometrium in order to avoid expulsion. The left horn remained intact.

After a week of rest the rabbits were mated. Ten days after mating, the occurrence of pregnancy was determined by observing the implantation sites through an abdominal incision. There were no implantations in the right uterine horn which contained the copper wire. There were, however, an average of 4.1 implantations per rabbit in the left uterine horn which had remained intact. This example illustrates clearly and definitely that copper serves as a potent antifertility agent when it lies in the endometrical cavity.

EXAMPLE 3

The contraceptive properties of metallic zinc were determined in experimental animals in the following manner:

Adult virginal rabbits were used. In each instance, the left uterine horn served as the control and the right uterine horn served as the site of the intrauterine device.

Under general anesthesia an abdominal incision was made and a 1.5 cm. length of zinc wire of 0.5 mm. diameter was inserted in the lower portion of the cavity of the right uterine horn close to the cervical os. The wire was fastened in place by a silk suture through the myometrium in order to avoid expulsion. The left horn remained intact.

After a week of rest the rabbits were mated. Ten days after mating, the occurrence of pregnancy was determined by observing the implantation sites through an abdominal incision. There were no implantations in the right uterine horn which contained the zinc wire. There were, however, an average of 3.5 implantations per rabbit in the left uterine horn which had remained intact. This example illustrates clearly and definitely that zinc serves as a potent antifertility agent when it lies in the endometrical cavity.

EXAMPLE 4

In order to illustrate that the contraceptive properties of copper are related to the amount of surface area of the copper which is exposed within the uterine cavity, the following experiment was performed.

Adult virginal rabbits were divided into two groups. Under general anesthesia and by the same surgical technique described in Examples 2 and 3, a single 1.5 cm. length of copper wire 0.20 mm. in diameter was affixed within the right uterine horn of the animals in Group A. The same procedure was followed in Group B except that four 1.5 cm. segments of copper wire 0.20 mm. in diameter were wound together and were affixed within the right uterine horn. The left uterine horns of all animals in both Groups A and B were kept intact and served as controls.

After a week of rest the rabbits were mated. Ten days after mating, the occurrence of pregnancy was determined by observing the implantation sites through an abdominal incision. There were no implantations in the right horns of the animals in Group B. There was no evidence of reduced implantation in the right or in the left horn of the animals in Group A. This example clearly illustrates that the contraceptive properties of copper are determined to some degree by the surface area of copper which is exposed within the uterine cavity.

EXAMPLE 5

The effectiveness of a two-metal system was studied by implantation of copper and silver couples in the rabbit uterus. The study as performed as follows:

Adult virginal rabbits were divided in four groups. Under general anesthesia the following foreign bodies were inserted in the lower portion of the cavity of the right uterine horn close to the cervical os. These were fastened in placed by a silk suture through the myometrium in order to avoid expulsion. In all four groups the left uterine horn was kept intact and thus served as the control. The foreign body affixed within the right uterine horn in the four groups was as follows:

Group A—a single copper wire 0.20 mm. diameter and 1.5 cm. long;

Group B—a single copper wire 0.20 mm. diameter and 1.5 cm. long wound around a silver wire 0.35 mm. diameter and 1.5 cm. long;

Group C—a silver wire 0.35 mm. diameter and 1.5 cm. long;

Group D—4 copper wires 0.20 mm. diameter and 1.5 cm. long.

After a week of rest the rabbits were mated. Ten days after mating, the occurrence of pregnancy was determined by observing the implantation sites through an abdominal incision. In Group A it was found that the presence of a single copper wire 0.20 mm. in diameter and 1.5 cm. long did not produce a marked effect on implantation rates in either the right uterine horn where the wire was implanted or in the contralateral horn. On the other hand, the presence of the two metals, i.e., Group B, with the same quantity of copper as in Group A, showed a remarkable decrease in the number of implantations in the right uterine horn where the two wires were placed. Implantations were normal in the contralateral horn. The silver wire used in Group C did not produce any effect on implantation rates. When the amount of copper was increased in Group D, no implantations were observed in the right uterine horn where the wires were placed. Implantations were normal in the contralateral horn. This example clearly illustrates that when two metals are mechanically combined and inserted in the uterine cavity, the contraceptive properties are greater than when one or the other metal is used alone.

I claim:

1. A method of contraception which comprises placing a contraceptively effective amount of an elemental metal selected from the group consisting of copper and zinc in the uterine cavity, *said elemental metal having an exposed surface area of at least about 20 square millimeters.*

2. A method as in claim 1 wherein a said elemental metal is attached to an intrauterine device effective to retain said metal in the uterine cavity over a prolonged period of time.

3. A method as in claim 1 wherein said metal is in the form of a pharmaceutically acceptable alloy.

[4. A method as in claim 1 wherein two dissimilar pharmaceutically acceptable metals are placed in the uterine cavity in contact with each other, at least one of said metals being selected from the group consisting of copper and zinc.]

[5. A method as in claim 4 wherein said dissimilar metals are silver and copper.]

[6. A method as in claim 1 wherein said elemental metal has an exposed surface area of at least about 20 square millimeters.]

7. An intrauterine contraceptive device adaptable to insertion in the uterine cavity and capable of being retained therein for prolonged periods of time, said device including a contraceptively effective amount of an elemental metal selected from the group consisting of copper and zinc, *and said elemental metal having an exposed surface area of at least about 20 square millimeters.*

[8. An intrauterine contraceptive device as in claim 7 wherein said elemental metal has an exposed surface area of at least about 20 square millimeters.]

References Cited

The following references, cited by the Examiner, are of record in the patented file of this patent or the original patent.

UNITED STATES PATENTS

| | | | |
|---|---|---|---|
| 559,406 | 5/1896 | Ryman | 128—131 |
| 662,716 | 11/1900 | Gaedeke | 128—130 |
| 454,573 | 6/1891 | Sherman | 128—131 |

| | | | |
|---|---|---|---|
| 709,675 | 9/1902 | Hollweg | 128—130 |
| 982,996 | 1/1911 | Rowell | 128—130 |
| 1,896,071 | 2/1933 | Clark | 128—130 |

OTHER REFERENCES

Intrauterine Devices for Contraception, The IUD, Hugh J. Davis, M.D., pp. 6, 7.

ALDRICH F. MEDBERY, Primary Examiner

U.S. Cl. X.R.

128—127